United States Patent [19]
Vaillancourt

[11] Patent Number: 4,715,854
[45] Date of Patent: Dec. 29, 1987

[54] MULTIDOSE DISPOSABLE SYRINGE AND METHOD OF FILLING SAME

[76] Inventor: Vincent L. Vaillancourt, 30A Ridgedale Ave., East Hanover, N.Y. 07936

[21] Appl. No.: 887,078

[22] Filed: Jul. 17, 1986

[51] Int. Cl.$^4$ .............................................. A61M 5/00
[52] U.S. Cl. ...................................... 604/191; 604/89; 604/122; 604/125; 604/208; 92/174; 141/2
[58] Field of Search ..................................... 604/89-91, 604/187, 191, 218, 238, 122, 124, 125, 903, 207, 208, 210; 92/61, 137, 174, 13.51; 141/2, 27

[56] References Cited

U.S. PATENT DOCUMENTS

| | | | |
|---|---|---|---|
| 1,733,057 | 8/1930 | Morefield | 92/137 |
| 3,598,120 | 8/1971 | Mass | 604/208 |
| 4,188,949 | 2/1980 | Antoshkiw | 604/191 |
| 4,246,898 | 1/1981 | Travalent et al. | |
| 4,439,184 | 3/1984 | Wheeler | 604/191 |
| 4,496,344 | 1/1985 | Kamstra | 604/191 |

FOREIGN PATENT DOCUMENTS

| | | | |
|---|---|---|---|
| 0730362 | 1/1943 | Fed. Rep. of Germany | 604/191 |
| 0529263 | 11/1921 | France | 604/207 |
| 0534030 | 3/1922 | France | 604/207 |
| 0796576 | 4/1936 | France | 604/207 |

*Primary Examiner*—C. Fred Rosenbaum
*Assistant Examiner*—Denise Whelton
*Attorney, Agent, or Firm*—Kenyon & Kenyon

[57] ABSTRACT

The multidose syringe is provided with two pistons which are attached by a string to move simultaneously. A groove in the barrel for delivering fluid into and from the innermost fluid chamber is provided with baffles to create turbulence in the fluid flow to preclude entry of air into the fluid chamber between the pistons during filling of the syringe.

9 Claims, 8 Drawing Figures

MULTIDOSE DISPOSABLE SYRINGE AND METHOD OF FILLING SAME

This invention relates to a multidose disposable syringe and to a method of filling the syringe.

Heretofore, various types of syringes have been known which are capable of dispensing multiple fluid doses. For example, U.S. Pat. No. 3,911,916 describes a sequential injection syringe of generally conventional structure in which a plug divides the interior of a barrel into two medicament receiving spaces. In addition, a cannula is provided with a conduit which extends into the barrel to pierce the plug during dispensing of the first medicament in order to provide a path for dispensing of the second medicament from the syringe. However, syringes of this type require some effort on the part of the user in order to have the conduit pierce the plug. In addition, there is a chance that the conduit may become blocked by debris from the plug during piercing of the plug so that the second medicament cannot be readily dispensed. Further, there is a risk that debris from the oierced plug may pass through the conduit into the cannula, and, thus, into a patient.

U.S. Pat. Nos. 4,235,235 and 4,496,344 describe syringes of single dose and double dose type, respectively. In both cases, a stopper is situated at the end of a cylindrical barrel over which a needle holder is secured by means of a snap-cap construction. In the double dose syringe, a piston is positioned in the barrel to define two fluid chambers. In order to use these syringes, a relatively large amount of pressure must be exerted on the pistons with the syringes and the column or columns of liquid therein in order to move the respective stoppers into the needle holder so that the liquids can be subsequently ejected. Further, it is difficult to fill these types of syringes with fluids in a convenient manner. For example, in the double dose syringe, if the stopper is initially placed in the end of the barrel, one liquid may be poured into the barrel and thereafter the pistion placed within the barrel so that the second liquid may be added. In any event, depending on the technique used to assemble the syringe, cumbersome filling steps must be taken in order to fill the syringes.

U.S. Pat. No. 4,439,184 describes a two-dose syringe having a fluid chamber in which two pistons are placed to define separate chambers for two fluids. In addition, the closed end of the tube is provided with a plurality of ridges in a by-pass zone of the tube adjacent to an output zone. These ridges serve to prevent the first piston from filling the cross-section of the by-pass zone so that fluid between the pistons can flow, or pass, around the first piston into the output zone. In an alternative embodiment, the by-pass zone may have grooves which are filled by the first piston so that fluid could flow around the piston once the piston has entered the by-pass zone. While there is no description as to how such a syringe may be filled, should a fluid be drawn into the syringe to pass about a piston, there is a possibility that air may also be drawn into the fluid chamber between the pistons. Should this occur, it become difficult and cumbersome to remove the air especially where the two fluids are to be dispensed sequentially without any interruption.

Accordingly, it is an object of the invention to provide a multidose disposable syringe in which the introduction of air into a fluid chamber is minimized.

It is another object of the invention to provide a multidose syringe having multiple pistons which can be moved simultaneously during filling in an accurate manner.

It is another object of the invention to be able to fill a multidose syringe in a reliable manner.

It is another object of the invention to be able to fill a multidose syringe with different fluids in a relatively easy manner.

Briefly, the invention provides a multidose disposable syringe and a method of filling a multidose syringe.

In one embodiment, the multidose syringe includes a one-piece cylindrical barrel having an open end and a tip defining a closed end with a duct extending therefrom as well as a pair of pistons which are mounted in the barrel in friction-fit relation to move from a position adjacent the closed end to respective positions spaced from the closed end in order to define two chambers for receiving respective fluids. The outermost piston, i.e., the piston furthest from the closed end, is also connected with a piston rod which extends from the barrel for subsequently dispensing the respective fluids from the syringe. In addition, a passageway is disposed between the innermost piston and the barrel in order to define a communicating path between the duct in the tip and a point between the pistons with the innermost piston in a position abutting the closed end.

Further, means are provided in the passageway to create turbulance in a flow of fluid drawn into the fluid chamber between the pistons during filling of the syringe in order to preclude an air flow into the chamber.

Of note, the introduction of air into the fluid chamber adjacent the tip is not critical since this air can be expelled at the time the syringe is to be used by a simple priming of the duct with fluid from the chamber, as is known. However, air which enters into the second chamber cannot be so removed, particularly, where the second fluid is to immediately follow the first fluid into a patient.

In addition, a collapsible means connects the two pistons so that the pistons move together after a predetermined movement of the outermost piston during filling. In this way, accurate amounts of fluid can be drawn into the respective fluid chambers.

In accordance with the invention, in order to fill the multidose disposable syringe, the pistons are initially positioned adjacent to the tip of the barrel. Thereafter, with the duct immersed in a fluid, the piston farthest from the tip is moved away from the closed end via the piston rod to form a first chamber between the pistons while drawing a fluid through the duct and passageway in the barrel into the chamber which is thus formed. After the first piston has moved a predetermined amount, drawing in of the fluid ceases and, then, both pistons are moved simultaneously away from the closed end in order to form a second chamber between the tip and the piston closest thereto. At that time, the duct is immersed in a second fluid so that the second fluid is drawn into the duct directly into the second chamber.

Since the pistons are interconnected by a collapsible means, the second fluid is drawn into the second chamber simultaneously with the simultaneous movement of the pistons during formation of the second chamber.

In a further embodiment, the pistons may be connected to separate means for withdrawing of each from the closed end of the barrel. For example, where the piston farthest from the closed end of the barrel is connected to a piston rod, the piston closest to the closed end of the barrel is connected to a collapsible means, such as a string, which passes through the piston farthest from the closed end of the barrel. In this case, the string can extend along the piston rod. In addition, in order to permit independent movement as well as adjustment of the space between the pistons, the string is removeably mounted in the free end of the piston rod and is provided with spaced apart stops so as to be held in one of a plurality of positions relative to the piston rod.

These and other objects and advantages of the invention will become more apparent from the following detailed description taken in conjunction with the accompanying drawings wherein.

Figure 1:
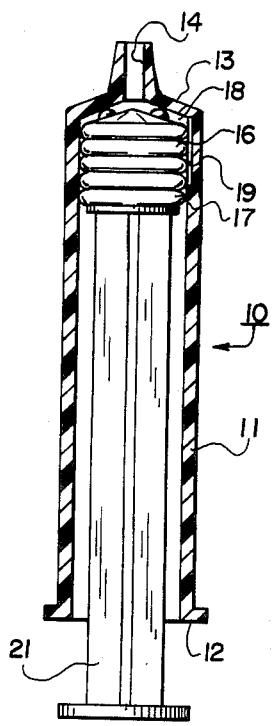
FIG. 1 illustrates a part cross-sectional view of a multidose syringe constructed in accordance with the invention.
Figure 2:
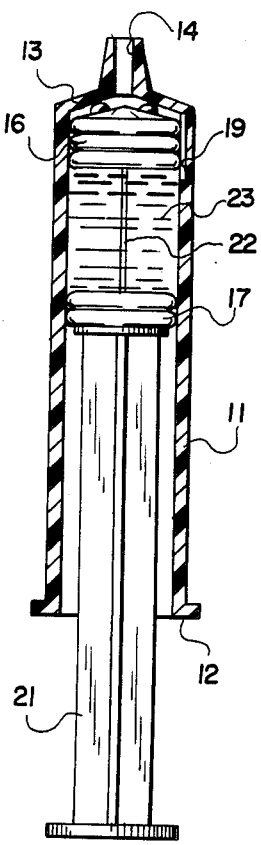
FIG. 2 illustrates a view similar to FIG. 1 during filling of the innermost chamber of the syringe.
Figure 3:
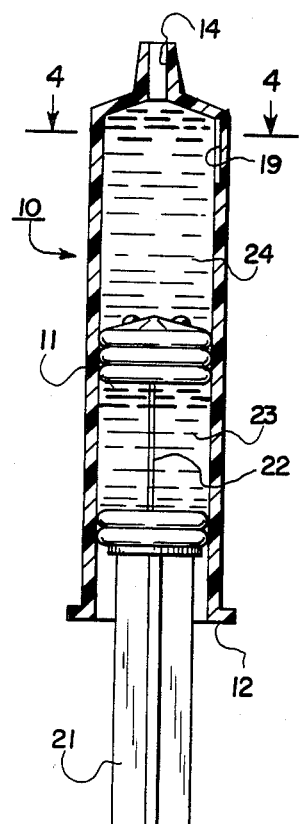
FIG. 3 illustrates a view similar to FIGS. 1 and 2 during filling of the outermost chamber of the syringe.

Referring to FIGS. 1 to 3, the multidose disposable syringe 10 is comprised of a one piece cylindrical barrel 11 having an open end 12 and a tip 13 defining a closed end with a duct 14 extending therefrom. This barrel 11 may be made of any conventional material suitable for syringes, the tip 13 is of conical shape while the duct 14 is centrally located on the axis of the barrel 11.

Figure 4:
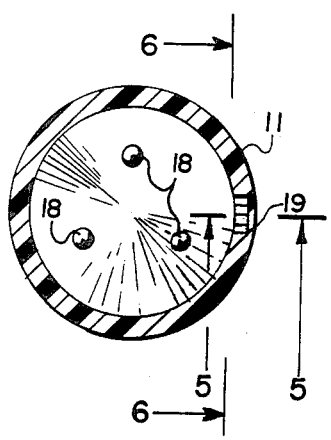
FIG. 4 illustrates a view taken on line 4—4 of FIG. 3.

In addition, a pair of pistons 16, 17 are slidably mounted in the barrel 11 in friction-fit relation. As indicated in FIG. 1, when the syringe 10 is empty, the pistons 16, 17 abut each other and are disposed at the closed end of the barrel 11. In addition, the piston 16 closest to the tip 13 has a plurality of protuberances 18, for example, in the form of beads (see FIG. 4) so as to provide a slight spacing or gap 18 between the piston 16 and the tip 13.

Figure 5:
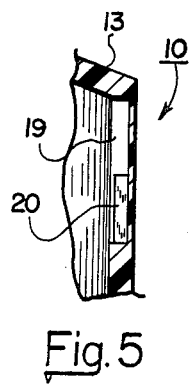
FIG. 5 illustrates a view taken on line 5—5 of FIG. 4.
Figure 6:
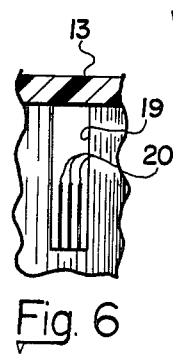
FIG. 6 illustrates a view taken on line 6—6 of FIG. 4.

A passageway 19, for example in the form of a groove in the barrel 11, extends over the length of the piston 16 when in the initial position indicated in FIG. 1 so as to define a communicating path between the duct 14 and a point between the pistons 16, 17 in the initial position. In addition, means, in the form of a plurality of parallel longitudinally disposed baffles 20 are disposed in the passageway 19 to create turbulance in a flow of fluid drawn into the passageway 19. As indicated in FIGS. 5 and 6, the baffles 20 extend along the rearmost half of the passageway 19 relative to the tip 13 of the syringe 10. By way of example, for a groove 19 of a width of 0.3 centimeters inside diameter (I.D.), three baffles are provided each of a length 0.5 centimeters and a thickness of 0.03 centimeters. These baffles may be formed by pressing a heated die (approximately 325° F.) pre configured to the male mating portion of the desired geometry. The plastic (normally polypropylene) is embossed and generates the desired configururation.

Referring to FIG. 2, a collapsible means in the form of a string 22 is secured to and between the pistons 16, 17. To this end, the piston 16 adjacent the tip 13 may be provided with a recess (not shown) to receive the collapsed string 22 when in the initial position indicated in FIG. 1. Alternatively, or in addition, the piston 17 farthest from the tip 13 may also be provided with a recess (not shown) to accommodate the collapsed string 22.

In order to fill the syringe 10, the duct 14 is placed in a reservoir of fluid (not shown) and the piston rod 20 withdrawn from the barrel 11. During this time, as indicated in FIG. 2, fluid is drawn through the duct 14 and the passageway 19 into a chamber 23 which forms between the pistons 16, 17 during withdrawal of the piston rod 21. As this fluid flows through the passageway 19, the baffles 20 create turbulence in the fluid flow so as to preclude an air inflow into the chamber 23 between the pistons 16, 17.

Referring to FIG. 2, after the outermost piston 17 has moved to a predetermined position in which the string 22 is pulled to a taut position, continued movement of the piston rod 21 causes the piston 16 adjacent the tip 13 to move. This movement is carried out for a short distance until the groove 19 is closed over by the piston 16 thus sealing the chamber 23 at both ends. At this time, the syringe 10 can be immersed into a second fluid and the piston rod 21 can then be drawn farther from the barrel 11 as indicated in FIG. 3. During this time, the second fluid is drawn into a chamber 24 which thus forms between the piston 16 and the tip 13. After the second chamber 24 has been filled to a predetermined amount, the duct 14 may be closed by any suitable means (not shown).

In order to use the syringe 10, the closure which is placed over the duct 14 is removed and/or pierced as the case may be by a cannula attachment or catheter tube (not shown) secured to a suitable means on the tip 13 of the barrel 11. Next, the fluid in the chamber 24 is dispensed by pushing the piston rod 21 into the barrel 11. During this time, the force imposed on the piston rod 21 is transferred via the piston 17, the fluid in the chamber 23 and the piston 16 onto the fluid in the chamber 24. In this regard, a simple manual force is required which is sufficient to overcome the friction of the pistons 16, 17 on the cylindrical wall of the barrel 11.

When the piston 16 abuts against the tip 13 via the protuberances 18, the passageway 19 opens the chamber 23 to the duct 14 so that the second fluid can then be dispensed from the syringe.

Figure 7:
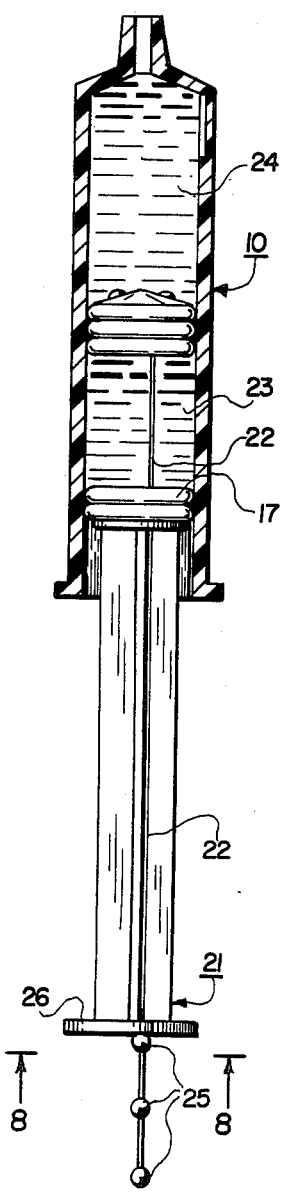
FIG. 7 illustrates a part cross-sectional view of a further modified syringe in accordance with the invention.
Figure 8:
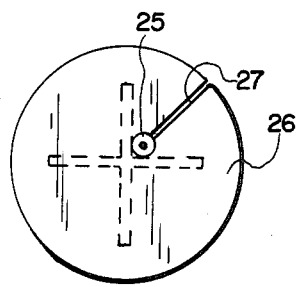
FIG. 8 illustrates a view taken on line 8—8 of FIG. 7.

Referring to FIGS. 7 and 8, wherein like reference characters indicate like parts as above, the syringe 10' has a string 22 which is secured in a suitable manner to one piston 16 while passing through the piston 17 to extend along the piston rod 21 to a point sufficient to permit independent movement of the pistons 16, 17 relative to each other. As indicated, the string 22 remains collapsible between the pistons 16, 17 and the free end is provided with a plurality of spaced apart stops 25 in the form of beads for engaging against a flange 26 on the piston rod 21 through which the string 22 passes via a slot 27 in the flange 26.

Initially, before filling of the disposable syringe 10", both pistons 16, 17 are at the closed end and the string 22 passes not only through one piston 17 but also through the slot 27 in the flange 26 of the piston rod 21. At this time, a free end of the string 22 is free to lie over the outside of the barrel 11. During withdrawal of the piston rod 21 to fill the first chamber 23, the flange 26 of the piston rod 21 slides along the free end of the string 22 until abutting the first stop 25. At this time, the first chamber 23 has reached a predetermined maximum fill. Any further withdrawal movement of the piston rod 21 would then cause both pistons 16, 17 to move simultaneously so as to create the second chamber 24. Thus, when the syringe 10" is exposed to a second fluid, the piston rod 21 is withdrawn to fill the second chamber 24.

Dispensing from the syringe 10" is the same as described above.

If a different amount of fluid is to be drawn into the first chamber 23, the string 22 may be moved from the slot 27 in the flange 26 and replaced at a point between two beads 25 so as to create a larger chamber 23.

The invention thus provides a multidose disposable syringe in which air may be prevented from entering into a fluid chamber between two pistons within the syringe barrel when the syringe is being filled.

Further, the invention provides a simple method of filling a multidose disposable syringe with multiple doses of fluid.

What is claimed is:

1. A multidose syringe comprising
   a one piece cylindrical barrel having an open end and a tip defining a closed end with a duct extending therefrom;
   a first piston mounted in said barrel in friction-fit relation to move from a first position abutting said closed end to a second position spaced therefrom to define a first chamber therebetween for receiving a first fluid;
   a second piston slidably mounted in said barrel in friction-fit relation to move between a first position adjacent said first piston and a second position spaced therefrom to define a second chamber therebetween for receiving a second fluid;
   a piston rod connected to said second piston and extending from said barrel;
   collapsible means connecting said pistons to move said first piston with said second piston after predetermined movement of said second piston from said first piston after filling of said second chamber with a fluid;
   a passageway disposed between said first piston and said barrel defining a communicating path between said duct and a point between said pistons with said first piston in said first position thereof; and
   means in said passageway to create turbulence in a flow of fluid drawn into said second chamber to preclude an air flow into said second chamber.

2. A multidose syringe as set forth in claim 1 wherein said passageway is disposed in said barrel.

3. A multidose syringe as set forth in claim 1 wherein said tip includes means for attaching a catheter tube about said duct.

4. A multidose syringe as set forth in claim 1 wherein said tip includes a concical end wall and said first piston has a plurality of protoberances thereon for abutting against said end wall in said first position thereof.

5. A multidose syringe as set forth in claim 1 where said means in said passageway includes a plurality of parallel longitudinally disposed baffles.

6. A multidose syringe comprising
   a barrel having an open end and a tip defining a duct at an opposite end;
   a piston rod disposed within and extending from said barrel;
   a first piston connected to said piston rod and slidably mounted in said barrel in friction-fit relation;
   at least a second piston mounted in said barrel between said first piston and said duct to move between a first position abutting said tip and a second position spaced from said tip to define a chamber therebetween to receive a fluid;
   a groove in said barrel defining a communicating path between said duct and a point between said pistons with said second piston abutting said tip in said first position; and
   collapsible means connecting said second piston to said first piston to move said second piston with said first piston after a predetermined movement of said first piston from said tip.

7. A multidose syringe as set forth in claim 6 wherein said collapsible means is a string secured to and between said pistons.

8. A multidose syringe as set forth in claim 7 wherein said string is secured to said second piston and slidably disposed in said first position.

9. A multidose syringe as set forth in claim 8 which further comprises a plurality of spaced apart stops on a free end of said strings, a flange on said piston rod and a slot in said flange slidably receiving said string with a selected one of said stops abutting said flange.

* * * * *

UNITED STATES PATENT AND TRADEMARK OFFICE
CERTIFICATE OF CORRECTION

PATENT NO. : 4,715,854

DATED : December 29, 1987

INVENTOR(S) : VINCENT L. VAILLANCOURT

It is certified that error appears in the above-identified patent and that said Letters Patent is hereby corrected as shown below:

Column 1, line 23 "oierced" should be - pierced-
Column 6, line 10 "concical" should be -conical- Signed and Sealed this Fourth Day of October, 1988

Attest:

DONALD J. QUIGG

*Attesting Officer*  *Commissioner of Patents and Trademarks*